United States Patent
Koizumi et al.

(10) Patent No.: US 9,738,681 B2
(45) Date of Patent: Aug. 22, 2017

(54) INTERMEDIATE FOR PRODUCTION OF NUCLEOSIDE ANALOG AND METHOD FOR PRODUCING THE SAME

(71) Applicant: Daiichi Sankyo Company, Limited, Tokyo (JP)

(72) Inventors: Makoto Koizumi, Tokyo (JP); Koji Morita, Tokyo (JP); Miho Sato, Tokyo (JP)

(73) Assignee: DAIICHI SANKYO COMPANY, LIMITED, Tokyo (JP)

(*) Notice: Subject to any disclaimer, the term of this patent is extended or adjusted under 35 U.S.C. 154(b) by 220 days.

(21) Appl. No.: 14/409,318

(22) PCT Filed: Jun. 17, 2013

(86) PCT No.: PCT/JP2013/066578
§ 371 (c)(1),
(2) Date: Dec. 18, 2014

(87) PCT Pub. No.: WO2013/191129
PCT Pub. Date: Dec. 27, 2013

(65) Prior Publication Data
US 2015/0152132 A1  Jun. 4, 2015
US 2016/0068561 A9  Mar. 10, 2016

(30) Foreign Application Priority Data

Jun. 18, 2012  (JP) ................. 2012-137049

(51) Int. Cl.
| C07H 19/00 | (2006.01) |
| C07H 19/22 | (2006.01) |
| C07H 23/00 | (2006.01) |
| C07F 7/10  | (2006.01) |
| C07H 19/16 | (2006.01) |

(52) U.S. Cl.
CPC ............ C07H 23/00 (2013.01); C07F 7/10 (2013.01); C07H 19/16 (2013.01); *Y02P 20/55* (2015.11)

(58) Field of Classification Search
CPC . C07H 23/00; C07H 19/16; C07F 7/10; Y02P 20/55
See application file for complete search history.

(56) References Cited

U.S. PATENT DOCUMENTS

| 7,314,923 B2* | 1/2008 | Kaneko | C07H 19/06 536/22.1 |
| 7,335,765 B2* | 2/2008 | Kaneko | C07H 19/06 536/22.1 |
| 7,651,999 B2* | 1/2010 | Koizumi | C07H 21/00 514/44 R |
| 7,816,333 B2* | 10/2010 | Kaneko | C07H 19/06 514/43 |
| 7,902,160 B2* | 3/2011 | Matsuo | C07H 21/04 514/44 R |
| 7,906,639 B2* | 3/2011 | Koizumi | C12Q 1/6853 435/91.2 |
| 7,994,152 B2* | 8/2011 | Koizumi | C07H 21/00 514/44 R |
| 8,541,562 B2 | 9/2013 | Obika et al. | |
| 8,624,019 B2* | 1/2014 | Matsuo | C07H 21/04 536/24.5 |
| 8,957,201 B2* | 2/2015 | Kaneko | C07H 19/06 536/22.1 |
| 9,243,026 B2* | 1/2016 | Matsuo | C07H 21/04 |
| 2013/0090465 A1* | 4/2013 | Matsuo | C07H 21/04 536/24.5 |
| 2016/0002636 A1* | 1/2016 | Matsuo | C07H 21/04 536/24.5 |

FOREIGN PATENT DOCUMENTS

| JP | 2000-297097 A | 10/2000 |
| WO | WO 2008/150729 A2 | 12/2008 |
| WO | WO 2011/052436 A1 | 5/2011 |

OTHER PUBLICATIONS

Mitsuoka et al., "Synthesis of 2',4'-BNA$^{COC}$ bearing a purine nucleobase," *Nucleic Acids Symposium Series No. 50*, (2006), pp. 13-14.
International Search Report issued on Jul. 30, 2013 in PCT Application No. PCT/JP2013/066578, 2 pages.

* cited by examiner

*Primary Examiner* — Lawrence E Crane
(74) *Attorney, Agent, or Firm* — Dorsey & Whitney LLP

(57) ABSTRACT

A compound represented by the general formula (III) which serves as an intermediate of an oligonucleotide analog having stable and excellent antisense or antigene activity or having excellent activity as a detection reagent (probe) for a specific gene or as a primer for the initiation of amplification of a specific gene can be produced at high yields regardless of the type of nucleobase by a method comprising reacting a compound represented by the general formula (II) or a salt thereof with a trimethylsilylated compound obtained from a compound represented by the general formula (IVb), wherein X, Y, Z, A, R, and B are as defined in claim 1.

14 Claims, No Drawings

INTERMEDIATE FOR PRODUCTION OF NUCLEOSIDE ANALOG AND METHOD FOR PRODUCING THE SAME

This application is a national stage application under 35 U.S.C. §371 of International Application No. PCT/JP2013/066578, filed Jun. 17, 2013, entitled "Intermediate for Production of Nucleoside Analogue, and Method for Producing Same," which claims priority to Japanese Patent Application No. 2012-137049, filed Jun. 18, 2012.

TECHNICAL FIELD

The present invention relates to a novel intermediate for production of a nucleoside analog which serves as an intermediate for production of an oligonucleotide analog having stable and excellent antisense or antigene activity or having excellent activity as a detection reagent (probe) for a specific gene or as a primer for initiation of amplification of a specific gene, and a method for producing the same.

BACKGROUND ART

Patent Literature 1 describes an oligonucleotide analog having stable and excellent antisense or antigene activity or having excellent activity as a detection reagent (probe) for a specific gene or as a primer for initiation of amplification of a specific gene, and the following nucleoside analog:

[Formula 1]

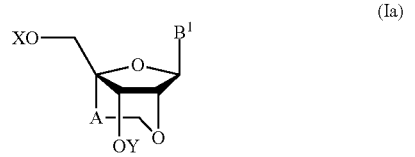

(Ia)

which serves as an intermediate for production of the oligonucleotide analog. The patent literature also describes steps A-3 and A-4 as a method for producing the nucleoside analog.

[Formula 2]

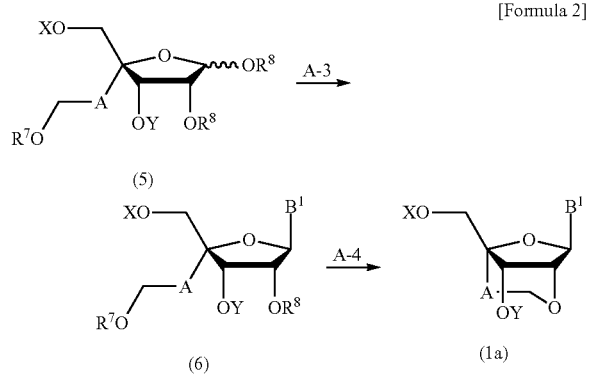

Patent Literature 1, however, makes no mention about a silyl protective group, though it specifically describes only an example wherein $R^7$ is a p-toluenesulfonyloxy group. Particularly, the production method described in Patent Literature 1 disadvantageously has a significantly reduced reaction yield, when the nucleobase is a 2-isobutyrylamino-6-hydroxypurin-9-yl group (yield of 6% in two steps of Reference Example 15 and Example 24). In addition, it is less than industrially satisfactory, even when the nucleobase is any of other groups, for example, when the nucleobase is a 6-benzoylaminopurin-9-yl group, the yield of step A-3 is as low as 52%.

Patent Literature 2 describes a nucleoside analog with the 2'- and 4'-positions bridged by a NHCOCH$_2$ group, and discloses the step of synthesizing compound 40 from compound 39 in Example 5(6).

[Formula 3]

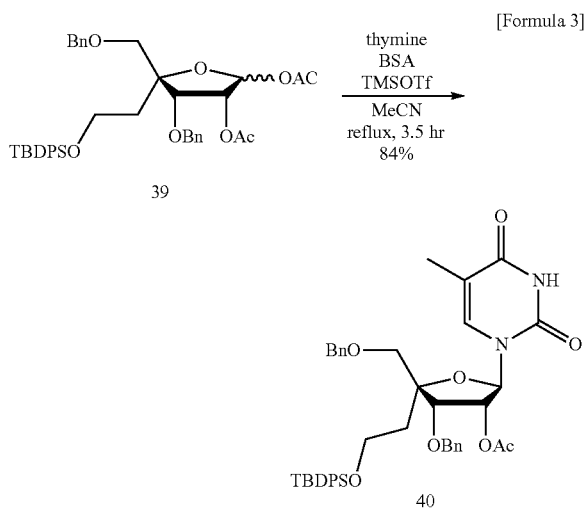

CITATION LIST

Patent Literature

Patent Literature 1: Japanese Patent Laid-Open No. 2000-297097
Patent Literature 2: International Publication No. WO2011/052436 A1

SUMMARY OF INVENTION

Technical Problem

Thus, the present inventors have conducted diligent studies to solve the problems mentioned above and consequently completed the present invention by finding that use of a production intermediate having a specific protective group can improve the reaction yield regardless of the type of nucleobase.

Solution to Problem

The production method of the present invention is a production method for producing a compound represented by the general formula (III) or a salt thereof, comprising reacting a trimethylsilylated compound, which was obtained by reaction of a compound represented by the following general formula:

[Formula 4]

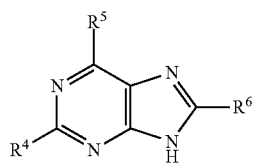

(IVb)

wherein $R^4$, $R^5$, and $R^6$ are the same or different and each represents a hydrogen atom, a hydroxy group, a protected hydroxy group, an alkoxy group having 1 to 4 carbon atoms, a mercapto group, a protected mercapto group, an alkylthio group having 1 to 4 carbon atoms, an amino group, a protected amino group, an amino group substituted by (an) alkyl group(s) having 1 to 4 carbon atoms, an alkyl group having 1 to 4 carbon atoms, or a halogen atom, with a trimethylsilylating agent,
with a compound represented by the following general formula:

[Formula 5]

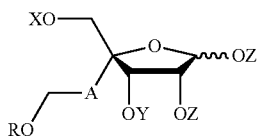

(II)

wherein X, Y, and Z are the same or different and each represents a protective group for the hydroxy group; A represents an alkylene group having 1 to 4 carbon atoms; and R represents a silyl protective group,
or a salt thereof:
to obtain the compound represented by the following general formula or a salt thereof:

[Formula 6]

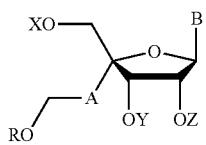

(III)

wherein X, Y, Z, A, and R are as defined above; and B represents a purin-9-yl group or a substituted purin-9-yl group having (a) substituent(s) selected from group α below.

The group α is a group consisting of a hydroxy group, a protected hydroxy group, an alkoxy group having 1 to 4 carbon atoms, a mercapto group, a protected mercapto group, an alkylthio group having 1 to 4 carbon atoms, an amino group, a protected amino group, an amino group substituted by (an) alkyl group(s) having 1 to 4 carbon atoms, an alkyl group having 1 to 4 carbon atoms, and a halogen atom.

The compound of the present invention is a compound represented by the above general formula (III) or a salt thereof.

Also, the production method of the present invention is a production method for producing a compound represented by the general formula (I) or a salt thereof, comprising the step of producing a compound represented by the general formula (III) or a salt thereof, the step comprising reacting a trimethylsilylated compound, which was obtained by reaction of a compound represented by the following general formula:

[Formula 7]

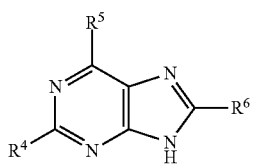

(IVb)

wherein $R^4$, $R^5$, and $R^6$ are as defined above,
with a trimethylsilylating agent,
with a compound represented by the following general formula:

[Formula 8]

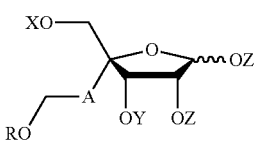

(II)

wherein X, Y, Z, A, and R are as defined above,
or a salt thereof:
to obtain the compound represented by the following general formula or a salt thereof:

[Formula 9]

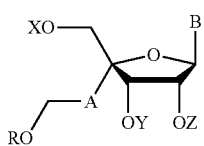

(III)

wherein X, Y, Z, A, R, and B are as defined above:

[Formula 10]

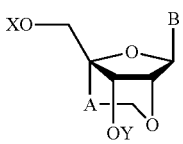

(I)

wherein X, Y, A, and B are as defined above.

In the present invention, examples of the "alkylene group having 1 to 4 carbon atoms" represented by A can include methylene, ethylene, trimethylene, and tetramethylene groups. The alkylene group is preferably a methylene or ethylene group, more preferably a methylene group.

In the present invention, the "protective group for the hydroxy group" represented by X, Y, or Z and the protective group in the "protected hydroxy group" included in the group α refer to protective groups that are cleavable by a chemical method such as hydrogenolysis, hydrolysis, electrolysis, or photolysis or by a biological method such as hydrolysis in the human body. Examples of such protective groups can include: "aliphatic acyl groups" such as alkylcarbonyl groups (e.g., formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and heneicosanoyl), carboxylated alkylcarbonyl groups (e.g., succinoyl, glutaroyl, and adipoyl), halogeno-lower alkylcarbonyl groups (e.g., chloroacetyl, dichloroacetyl, trichloroacetyl, and trifluoroacetyl), lower alkoxy lower alkylcarbonyl groups (e.g., methoxyacetyl), and unsaturated alkylcarbonyl groups (e.g., (E)-2-methyl-2-butenoyl); "aromatic acyl groups" such as arylcarbonyl groups (e.g., benzoyl, α-naphthoyl, and β-naphthoyl), halogenoarylcarbonyl groups (e.g., 2-bromobenzoyl and 4-chlorobenzoyl), lower alkylated arylcarbonyl groups (e.g., 2,4,6-trimethylbenzoyl and 4-toluoyl), lower alkoxylated arylcarbonyl groups (e.g., 4-anisoyl), carboxylated arylcarbonyl groups (e.g., 2-carboxybenzoyl, 3-carboxybenzoyl, and 4-carboxybenzoyl), nitrated arylcarbonyl groups (e.g., 4-nitrobenzoyl and 2-nitrobenzoyl), lower alkoxycarbonylated arylcarbonyl groups (e.g., 2-(methoxycarbonyl)benzoyl), and arylated arylcarbonyl groups (e.g., 4-phenylbenzoyl); "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl; "tetrahydrofuranyl or tetrahydrothiofuranyl groups" such as tetrahydrofuran-2-yl and tetrahydrothiofuran-2-yl; "lower alkoxymethyl groups" such as methoxymethyl, 1,1-dimethyl-1-methoxymethyl, ethoxymethyl, propoxymethyl, isopropoxymethyl, butoxymethyl, and t-butoxymethyl; "lower alkoxylated lower alkoxymethyl groups" such as 2-methoxyethoxymethyl; "halogeno-lower alkoxymethyl" such as 2,2,2-trichloroethoxymethyl and bis(2-chloroethoxy)methyl; "lower alkoxylated ethyl groups" such as 1-ethoxyethyl and 1-(isopropoxy)ethyl; "halogenated ethyl groups" such as 2,2,2-trichloroethyl; a "methyl group substituted by 1 to 3 aryl groups" such as benzyl, α-naphthylmethyl, β-naphthylmethyl, diphenylmethyl, triphenylmethyl, α-naphthyldiphenylmethyl, and 9-anthrylmethyl; a "methyl group substituted by 1 to 3 aryl groups with the aryl ring substituted by lower alkyl, lower alkoxy, halogen, or a cyano group" such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, and 4-cyanobenzyl; "lower alkoxycarbonyl groups" such as methoxycarbonyl, ethoxycarbonyl, t-butoxycarbonyl, and isobutoxycarbonyl; "halogen-substituted lower alkoxycarbonyl groups" such as 2,2,2-trichloroethoxycarbonyl; "alkenyloxycarbonyl groups" such as vinyloxycarbonyl and aryloxycarbonyl; and "aralkyloxycarbonyl groups with the aryl ring optionally substituted by 1 or 2 lower alkoxy or nitro groups" such as benzyloxycarbonyl, 4-methoxybenzyloxycarbonyl, 3,4-dimethoxybenzyloxycarbonyl, 2-nitrobenzyloxycarbonyl, and 4-nitrobenzyloxycarbonyl. The "protective group for the hydroxy group" represented by X or Y is preferably a "methyl group substituted by 1 to 3 aryl groups" or a "methyl group substituted by 1 to 3 aryl groups with the aryl ring substituted by lower alkyl, lower alkoxy, halogen, or a cyano group", more preferably a benzyl, β-naphthylmethyl, p-methoxybenzyl, dimethoxytrityl, or monomethoxytrityl group. The "protective group for the hydroxy group" represented by Z is preferably an aliphatic acyl group having 2 to 4 carbon atoms (e.g., an acetyl, propionyl, or butyryl group), more preferably an acetyl group. The "protected hydroxy group" included in the group α is preferably an "ethyl group substituted by a nitrated aryl group" or an "arylated aminocarbonyl group", more preferably a 1-(4-nitrophenyl)ethyl group or a diphenylaminocarbonyl group.

In the present invention, the "silyl protective group" represented by R can be a "silyl protective group" such as a tri-lower alkylsilyl group (e.g., trimethylsilyl, triethylsilyl, isopropyldimethylsilyl, t-butyldimethylsilyl, methyldiisopropylsilyl, methyl-di-t-butylsilyl, or triisopropylsilyl); or a monoaryl di-lower alkylsilyl or diaryl mono-lower alkylsilyl group (e.g., diphenylmethylsilyl, diphenylbutylsilyl, diphenylisopropylsilyl, t-butyldiphenylsilyl, or phenyldiisopropylsilyl). The silyl protective group is preferably a monoaryl di-lower alkylsilyl or diaryl mono-lower alkylsilyl group, more preferably a t-butyldiphenylsilyl group.

In the present invention, examples of the "alkoxy group having 1 to 4 carbon atoms" included in the group α can include methoxy, ethoxy, n-propoxy, isopropoxy, n-butoxy, isobutoxy, s-butoxy, and t-butoxy groups. The alkoxy group is preferably a methoxy or ethoxy group.

In the present invention, examples of the protective group in the "protected mercapto group" included in the group α can include those listed above as the protective group for the hydroxy group as well as "disulfide-forming groups" such as alkylthio groups (e.g., methylthio, ethylthio, and t-butylthio) and arylthio groups (e.g., benzylthio). The protective group is preferably an "aliphatic acyl group" or an "aromatic acyl group", more preferably a benzoyl group.

In the present invention, examples of the "alkylthio group having 1 to 4 carbon atoms" included in the group α can include methylthio, ethylthio, propylthio, isopropylthio, butylthio, isobutylthio, s-butylthio, and t-butylthio groups. The alkylthio group is preferably a methylthio or ethylthio group.

In the present invention, examples of the protective group in the "protected amino group" included in the group α can include: "aliphatic acyl groups" such as alkylcarbonyl groups (e.g., formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and heneicosanoyl), carboxylated alkylcarbonyl groups (e.g., succinoyl, glutaroyl, and adipoyl), halogeno-lower alkylcarbonyl groups (e.g., chloroacetyl, dichloroacetyl, trichloroacetyl, and trifluoroacetyl), lower alkoxy lower alkylcarbonyl groups (e.g., methoxyacetyl), aryloxy lower alkylcarbonyl groups (e.g., a phenoxyacetyl group), aryloxy lower alkylcarbonyl groups (e.g., a 4-(t-butyl)phenoxyacetyl group), and unsaturated alkylcarbonyl groups (e.g., (E)-2-methyl-2-butenoyl); "aromatic acyl groups" such as arylcarbonyl groups (e.g., benzoyl, α-naphthoyl, and β-naphthoyl), halogenoarylcarbonyl groups (e.g., 2-bromobenzoyl and 4-chlorobenzoyl), lower alkylated arylcarbonyl groups (e.g., 2,4,6-trimethylbenzoyl and 4-toluoyl), lower alkoxylated arylcarbonyl groups (e.g., 4-anisoyl), carboxylated arylcarbonyl groups (e.g., 2-carboxybenzoyl, 3-carboxybenzoyl, and 4-carboxybenzoyl), nitrated arylcarbonyl groups (e.g., 4-nitrobenzoyl and 2-nitrobenzoyl), lower alkoxycarbonylated arylcarbonyl groups (e.g., 2-(methoxycarbonyl)benzoyl), and arylated arylcarbonyl groups (e.g., 4-phenylbenzoyl); "lower alkoxycarbonyl groups" such as methoxycarbonyl, ethoxycarbonyl, t-butoxycarbonyl, and isobutoxycarbonyl; "lower alkoxycarbonyl groups substituted by halogen or a tri-lower alkylsilyl group" such as 2,2,2-trichloroethoxycarbonyl and 2-trimethylsilylethoxycarbonyl; "alkenyloxycarbonyl groups" such as vinyloxycarbonyl and aryloxycarbonyl; and "aralkyloxycarbonyl groups with the aryl ring optionally substituted by 1 or 2 lower alkoxy or nitro groups" such as benzyloxycarbonyl, 4-methoxybenzyloxycarbonyl, 3,4-dimethoxybenzyloxycarbonyl, 2-nitrobenzyloxycarbonyl, and 4-nitrobenzyloxycarbonyl. The protective group is preferably an "aliphatic acyl group" or an "aromatic acyl group", more preferably an isobutyryl or benzoyl group, most preferably an isobutyryl group.

In the present invention, examples of the "amino group substituted by (an) alkyl group(s) having 1 to 4 carbon atoms" included in the group α can include methylamino, ethylamino, propylamino, isopropylamino, butylamino, isobutylamino, s-butylamino, t-butylamino, dimethylamino, diethylamino, dipropylamino, diisopropylamino, dibutylamino, diisobutylamino, di(s-butyl)amino, and di(t-butyl) amino groups. The amino group substituted by (an) alkyl group(s) is preferably a methylamino, ethylamino, dimethylamino, diethylamino, or diisopropylamino group.

In the present invention, examples of the "alkyl group having 1 to 4 carbon atoms" included in the group α can include methyl, ethyl, propyl, isopropyl, butyl, isobutyl, s-butyl, and t-butyl. The alkyl group is preferably a methyl or ethyl group.

In the present invention, the "halogen atom" included in the group α refers to a fluorine atom, a chlorine atom, a bromine atom, or an iodine atom and is preferably a fluorine atom or a chlorine atom.

In the present invention, the "purin-9-yl group" or the "substituted purin-9-yl group" represented by B is preferably a 6-aminopurin-9-yl (i.e., adeninyl) group, a 6-aminopurin-9-yl group with the amino group protected, a 2,6-diaminopurin-9-yl group, a 2-amino-6-chloropurin-9-yl group, a 2-amino-6-chloropurin-9-yl group with the amino group protected, a 2-amino-6-fluoropurin-9-yl group, a 2-amino-6-fluoropurin-9-yl group with the amino group protected, a 2-amino-6-bromopurin-9-yl group, a 2-amino-6-bromopurin-9-yl group with the amino group protected, a 2-amino-6-hydroxypurin-9-yl (i.e., guaninyl) group, a 2-amino-6-hydroxypurin-9-yl group with the amino group protected, a 2-amino-6-hydroxypurin-9-yl group with the amino group and hydroxy group protected, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, or a 6-mercaptopurin-9-yl group, more preferably a 6-benzoylaminopurin-9-yl group, an adeninyl group, a 2-isobutyrylamino-6-hydroxypurin-9-yl group, or a guaninyl group.

In the present invention, the "salt thereof" refers to a salt of compound (II) or (III), because these compounds can form salts. Such salts can be preferably metal salts such as alkali metal salts (e.g., sodium salt, potassium salt, and lithium salt), alkaline earth metal salts (e.g., calcium salt and magnesium salt), aluminum salt, iron salt, zinc salt, copper salt, nickel salt, and cobalt salt; amine salts such as inorganic salts (e.g., ammonium salt) and organic salts (e.g., t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt, and tris(hydroxymethyl)aminomethane salt); inorganic acid salts such as hydrohalides (e.g., hydrofluoride, hydrochloride, hydrobromide, and hydroiodide), nitrate, perchlorate, sulfate, and phosphate; organic acid salts such as lower alkanesulfonates (e.g., methanesulfonate, trifluoromethanesulfonate, and ethanesulfonate), arylsulfonates (e.g., benzenesulfonate and p-toluenesulfonate), acetate, malate, fumarate, succinate, citrate, tartrate, oxalate, and maleate; and amino acid salts such as glycine salt, lysine salt, arginine salt, ornithine salt, glutamate, and aspartate.

Preferred embodiments of the production method of the present invention are as follows:

(1) The production method, wherein X is a methyl group substituted by 1 to 3 aryl groups, or a methyl group substituted by 1 to 3 aryl groups with the aryl ring substituted by lower alkyl, lower alkoxy, halogen, or a cyano group.

(2) The production method, wherein X is a benzyl group, a p-methoxybenzyl group, a dimethoxytrityl group, or a monomethoxytrityl group.

(3) The production method, wherein Y is a methyl group substituted by 1 to 3 aryl groups, or a methyl group substituted by 1 to 3 aryl groups with the aryl ring substituted by lower alkyl, lower alkoxy, halogen, or a cyano group.

(4) The production method, wherein Y is a benzyl group, a β-naphthylmethyl group, or a p-methoxybenzyl group.

(5) The production method, wherein Z is an aliphatic acyl group having 2 to 4 carbon atoms.

(6) The production method, wherein Z is an acetyl group.

(7) The production method, wherein A is a methylene group or an ethylene group.

(8) The production method, wherein A is a methylene group.

(9) The production method, wherein B is a 6-aminopurin-9-yl (i.e., adeninyl) group, a 6-aminopurin-9-yl group with the amino group protected, a 2,6-diaminopurin-9-yl group, a 2-amino-6-chloropurin-9-yl group, a 2-amino-6-chloropurin-9-yl group with the amino group protected, a 2-amino-6-fluoropurin-9-yl group, a 2-amino-6-fluoropurin-9-yl group with the amino group protected, a 2-amino-6-bromopurin-9-yl group, a 2-amino-6-bromopurin-9-yl group with the amino group protected, a 2-amino-6-hydroxypurin-9-yl (i.e., guaninyl) group, a 2-amino-6-hydroxypurin-9-yl group with the amino group protected, a 2-amino-6-hydroxypurin-9-yl group with the amino group and hydroxy group protected, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, or a 6-mercaptopurin-9-yl group.

(10) The production method, wherein B is a 6-benzoylaminopurin-9-yl group, an adeninyl group, a 2-isobutyrylamino-6-hydroxypurin-9-yl group, or a guaninyl group.

(11) The production method, wherein R is a tri-lower alkylsilyl group, a monoaryl di-lower alkylsilyl group, or a diaryl mono-lower alkylsilyl group.

(12) The production method, wherein R is a monoaryl di-lower alkylsilyl group or a diaryl mono-lower alkylsilyl group.

(13) The production method, wherein R is a t-butyldiphenylsilyl group.

The larger number between or among (1) and (2), (3) and (4), (5) and (6), (7) and (8), (9) and (10), or (11) to (13) mentioned above represents a more preferred embodiment of the production method. The production method of the present invention is also preferably a production method, wherein X is arbitrarily selected from (1) and (2); Y is arbitrarily selected from (3) and (4); Z is arbitrarily selected from (5) and (6); A is arbitrarily selected from (7) and (8); B is arbitrarily selected from (9) and (10); or R is arbitrarily selected from (11) to (13); or these forms are arbitrarily combined.

Preferred embodiments of the compound (III) of the present invention are as follows:

(1) The compound or a salt thereof, wherein X is a methyl group substituted by 1 to 3 aryl groups, or a methyl group substituted by 1 to 3 aryl groups with the aryl ring substituted by lower alkyl, lower alkoxy, halogen, or a cyano group.

(2) The compound or a salt thereof, wherein X is a benzyl group, a p-methoxybenzyl group, a dimethoxytrityl group, or a monomethoxytrityl group.

(3) The compound or a salt thereof, wherein Y is a methyl group substituted by 1 to 3 aryl groups, or a methyl group substituted by 1 to 3 aryl groups with the aryl ring substituted by lower alkyl, lower alkoxy, halogen, or a cyano group.

(4) The compound or a salt thereof, wherein Y is a benzyl group, a β-naphthylmethyl group, or a p-methoxybenzyl group.

(5) The compound or a salt thereof, wherein Z is an aliphatic acyl group having 2 to 4 carbon atoms.

(6) The compound or a salt thereof, wherein Z is an acetyl group.

(7) The compound or a salt thereof, wherein A is a methylene group or an ethylene group.

(8) The compound or a salt thereof, wherein A is a methylene group.

(9) The compound or a salt thereof, wherein B is a 6-aminopurin-9-yl (i.e., adeninyl) group, a 6-aminopurin-9-yl group with the amino group protected, a 2,6-diaminopurin-9-yl group, a 2-amino-6-chloropurin-9-yl group, a 2-amino-6-chloropurin-9-yl group with the amino group protected, a 2-amino-6-fluoropurin-9-yl group, a 2-amino-6-fluoropurin-9-yl group with the amino group protected, a 2-amino-6-bromopurin-9-yl group, a 2-amino-6-bromopurin-9-yl group with the amino group protected, a 2-amino-6-hydroxypurin-9-yl (i.e., guaninyl) group, a 2-amino-6-hydroxypurin-9-yl group with the amino group protected, a 2-amino-6-hydroxypurin-9-yl group with the amino group and hydroxy group protected, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, or a 6-mercaptopurin-9-yl group.

(10) The compound or a salt thereof, wherein B is a 6-benzoylaminopurin-9-yl group, an adeninyl group, a 2-isobutyrylamino-6-hydroxypurin-9-yl group, or a guaninyl group.

(11) The compound or a salt thereof, wherein R is a tri-lower alkylsilyl group, a monoaryl di-lower alkylsilyl group, or a diaryl mono-lower alkylsilyl group.

(12) The compound or a salt thereof, wherein R is a monoaryl di-lower alkylsilyl group or a diaryl mono-lower alkylsilyl group.

(13) The compound or a salt thereof, wherein R is a t-butyldiphenylsilyl group.

The larger number between or among (1) and (2), (3) and (4), (5) and (6), (7) and (8), (9) and (10), or (11) to (13) mentioned above represents a more preferred embodiment of the compound. The production intermediate of the present invention is also preferably a compound or a salt thereof, wherein X is arbitrarily selected from (1) and (2); Y is arbitrarily selected from (3) and (4); Z is arbitrarily selected from (5) and (6); A is arbitrarily selected from (7) and (8); B is arbitrarily selected from (9) and (10); or R is arbitrarily selected from (11) to (13); or these forms are arbitrarily combined, particularly preferably 2'-O-acetyl-3',5'-di-O-benzyl-4'-(2-t-butyldiphenylsilyloxyethyl)-6-N-benzoyladenosine, 2'-O-acetyl-3',5'-di-O-benzyl-4'-(2-t-butyldiphenylsilyloxyethyl)-2-N-isobutyrylguanosine, or a salt thereof, most preferably 2'-O-acetyl-3',5'-di-O-benzyl-4'-(2-t-butyldiphenylsilyloxyethyl)-2-N-isobutyrylguanosine or a salt thereof.

The compound (IVb) is purine, or substituted purine optionally having a substituent selected from the group consisting of (a) hydroxy group(s), (a) protected hydroxy group(s), (an) alkoxy group(s) having 1 to 4 carbon atoms, (a) mercapto group(s), (a) protected mercapto group(s), (an) alkylthio group(s) having 1 to 4 carbon atoms, (an) amino group(s), (a) protected amino group(s), (an) amino group(s) substituted by (an) alkyl group(s) having 1 to 4 carbon atoms, (an) alkyl group(s) having 1 to 4 carbon atoms, and (a) halogen atom(s) and is preferably a compound or a salt thereof selected from the following group:

(Compound Group)

Adenine with the amino group protected, guanine with the amino group protected, and salts thereof, preferably adenine with the amino group protected with an "aliphatic acyl group" or an "aromatic acyl group", guanine with the amino group protected with an "aliphatic acyl group" or an "aromatic acyl group", and salts thereof, more preferably N6-benzoyladenine, N6-acetyladenine, N6-phenoxyacetyladenine, N6-(t-butyl)phenoxyacetyladenine, N2-isobutyrylguanine, N2-acetylguanine, N2-phenoxyacetylguanine, N2-(t-butyl)phenoxyacetylguanine, and salts thereof, even more preferably N6-benzoyladenine, N2-isobutyrylguanine, and salts thereof.

The trimethylsilylated compound according to the present invention refers to a compound that is produced through the reaction of compound (IVb) with a trimethylsilylating agent resulting in the bonding of a trimethylsilyl group in place of a hydrogen atom bonded to a nitrogen atom of an amino group, a hydrogen atom bonded to a nitrogen atom in the heterocyclic ring and/or a hydrogen atom bonded to an oxygen atom of a hydroxy group in the compound (IVb). The trimethylsilylated compound is relatively unstable and is therefore used in the subsequent reaction without being isolated. The trimethylsilylated compound is preferably a compound in which a trimethylsilyl group is bonded in place of a hydrogen atom bonded to a nitrogen atom of an amino group, a hydrogen atom bonded to a nitrogen atom in the heterocyclic ring and/or a hydrogen atom bonded to an oxygen atom of a hydroxy group, in an adenine in which the amino group is protected with an "aliphatic acyl group" or an "aromatic acyl group" or a guanine in which the amino group is protected with an "aliphatic acyl group" or an "aromatic acyl group", or a salt thereof, more preferably a compound in which a trimethylsilyl group is bonded in place of a hydrogen atom bonded to a nitrogen atom of an amino group, a hydrogen atom bonded to a nitrogen atom in the heterocyclic ring and/or a hydrogen atom bonded to an oxygen atom of a hydroxy group, in an N6-benzoyladenine, N6-acetyladenine, N6-phenoxyacetyladenine, N6-(t-butyl)phenoxyacetyladenine, N2-isobutyrylguanine, N2-acetylguanine, N2-phenoxyacetylguanine, or N2-(t-butyl)phenoxyacetylguanine, or a salt thereof, particularly preferably a compound in which a trimethylsilyl group is bonded in place of a hydrogen atom bonded to a nitrogen atom of an amino group, a hydrogen atom bonded to a nitrogen atom in the heterocyclic ring and/or a hydrogen atom bonded to an oxygen atom of a hydroxy group, in an N6-benzoyladenine or N2-isobutyrylguanine, or a salt thereof.

The trimethylsilylated compound is, for example, N6-benzoyl-N6,N9-bis(trimethylsilyl)adenine or O6,N2,N9-tris(trimethylsilyl)-N2-isobutyrylguanine.

The compound (III), the compound (IVb), or the trimethylsilylated compound of the compound (IVb) according to the present invention may have tautomerism. Any tautomeric structure of the following substructure in these compounds is included in the scope of the present invention:

[Formula 11]

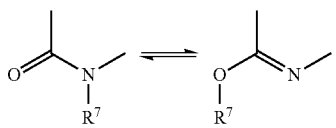

wherein $R^7$ represents a hydrogen, a protective group for the hydroxy group, a protective group for the amino group, or a trimethylsilyl group.

Advantageous Effects of Invention

According to the present invention, an oligonucleotide analog having stable and excellent antisense or antigene activity or having excellent activity as a detection reagent (probe) for a specific gene or as a primer for initiation of amplification of a specific gene, and intermediate compound (III) for the production of nucleoside analog compound (I) which serves as an intermediate for the production thereof can be produced at high yields regardless of the type of nucleobase.

DESCRIPTION OF EMBODIMENTS

The production method of the present invention is a method for producing compound (III), comprising reacting compound (IVb) with a trimethylsilylating agent, and then reacting the obtained trimethylsilylated compound with compound (II).

wherein $R^4$, $R^5$, $R^6$, X, Y, Z, A, R, and B are as defined above.

(1) Step of Producing Compound (II)

Compound (II), which is a starting material in this step, can be produced through the reaction of compound (3) of method A described in Japanese Patent Laid-Open No. 2000-297097 with a silyl protecting agent in the presence of a base catalyst in an inert solvent.

The silyl protecting agent used is a tri-lower alkylsilyl chloride such as trimethylsilyl chloride, triethylsilyl chloride, isopropyldimethylsilyl chloride, t-butyldimethylsilyl chloride, methyldiisopropylsilyl chloride, methyl-di-t-butylsilyl chloride, or triisopropylsilyl chloride; or a monoaryl di-lower alkylsilyl or diaryl mono-lower alkylsilyl chloride such as diphenylmethylsilyl chloride, diphenylbutylsilyl chloride, diphenylisopropylsilyl chloride, t-butyldiphenylsilyl chloride, or phenyldiisopropylsilyl chloride.

Examples of the solvent used can include: aromatic hydrocarbons such as benzene, toluene, and xylene; halogenated hydrocarbons such as methylene chloride, chloroform, carbon tetrachloride, 1,2-dichloroethane, chlorobenzene, and dichlorobenzene; nitriles such as acetonitrile and isobutyronitrile; amides such as formamide, N,N-dimethylformamide, N,N-dimethylacetamide, N-methyl-2-pyrrolidone, N-methylpyrrolidinone, and hexamethylphosphortriamide; and carbon sulfide. The solvent is preferably N,N-dimethylformamide.

Examples of the base catalyst used include organic bases such as triethylamine, pyridine, N-methylmorpholine, DBU, and imidazole. The base catalyst is preferably imidazole.

The reaction temperature differs depending on the starting compound, solvent, and base catalyst used and is usually 0° C. to 100° C., preferably 0° C. to 50° C.

The reaction time differs depending on the starting compound, solvent, and base catalyst used, and the reaction temperature and is usually 0.5 hours to 24 hours, preferably 1 hour to 8 hours.

After the completion of the reaction, the compound (II) of interest of this reaction is obtained, for example, by: concentrating the reaction mixture; adding water and an immiscible organic solvent such as ethyl acetate to the residue; after washing with water, separating the organic layer containing the compound of interest; drying the organic layer over anhydrous magnesium sulfate or the like; and then distilling off the solvent.

The obtained compound can be further purified, if necessary, by a routine method, for example, recrystallization or silica gel column chromatography.

[Formula 12]

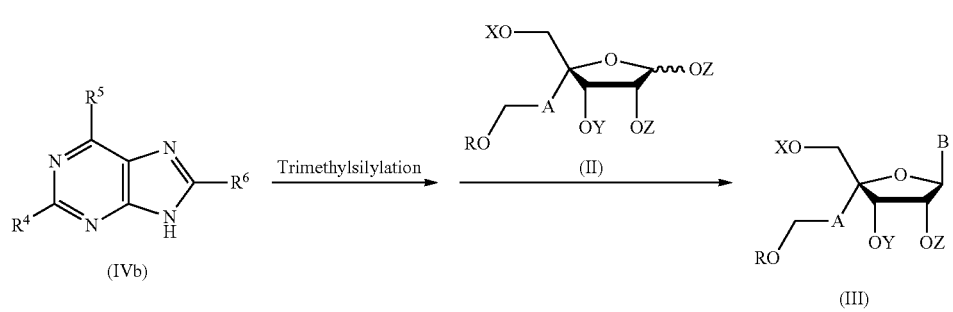

(2) Step of Producing Trimethylsilylated Compound

The trimethylsilylated compound used in this step can be produced through the reaction of compound (IVb) with a trimethylsilylating agent.

The trimethylsilylating agent used can be trimethylsilyl chloride, N,O-bis(trimethylsilyl)acetamide (BSA), N,O-bis(trimethylsilyl)trifluoroacetamide, N-methyl-N-(trimethylsilyl)trifluoroacetamide, 1,1,1,3,3,3-hexamethyldisilazane (HMDS), or trimethylsilyl trifluoromethanesulfonate and is preferably trimethylsilyl chloride or N,O-bis(trimethylsilyl)acetamide (BSA).

The trimethylsilylating agent is usually used at 1 to 100 equivalents, preferably 2 to 50 equivalents, particularly preferably 5 to 30 equivalents, with respect to one reaction site of 1 to 4 hydrogen atoms bonded to a nitrogen atom of the N—H group or an oxygen atom of a hydroxy group in the compound (IVb).

Examples of the solvent used can include: aromatic hydrocarbons such as benzene, toluene, and xylene; halogenated hydrocarbons such as methylene chloride, chloroform, carbon tetrachloride, 1,2-dichloroethane, chlorobenzene, and dichlorobenzene; nitriles such as acetonitrile and isobutyronitrile; amides such as formamide, N,N-dimethylformamide, N,N-dimethylacetamide, N-methyl-2-pyrrolidone, N-methylpyrrolidinone, and hexamethylphosphortriamide; 1,1,1,3,3,3-hexamethyldisilazane (HMDS); and carbon sulfide. The solvent is preferably toluene, acetonitrile, or HMDS.

In this step, for example, an organic base such as triethylamine, pyridine, N-methylmorpholine, DBU, or imidazole may be used as a base catalyst according to the need. The base catalyst is preferably triethylamine.

The reaction temperature differs depending on the starting compound, solvent, and base catalyst used and is usually 0° C. to 180° C., preferably 20° C. to 120° C.

After the completion of the reaction, the compound of interest of this reaction is used in the subsequent step without being isolated, for example, after concentration of the reaction mixture and drying of the residue under reduced pressure.

(3) Step of Producing Compound (III)

This step involves reacting the said trimethylsilylated compound with the said compound (II) in the presence of an acid catalyst in an inert solvent to produce compound (III).

Examples of the solvent used can include: aromatic hydrocarbons such as benzene, toluene, and xylene; halogenated hydrocarbons such as methylene chloride, chloroform, carbon tetrachloride, 1,2-dichloroethane, chlorobenzene, and dichlorobenzene; nitriles such as acetonitrile and isobutyronitrile; amides such as formamide, N,N-dimethylformamide, N,N-dimethylacetamide, N-methyl-2-pyrrolidone, N-methylpyrrolidinone, and hexamethylphosphortriamide; and carbon sulfide. The solvent is preferably an aromatic hydrocarbon or a nitrile, more preferably toluene or acetonitrile.

Examples of the acid catalyst used include Lewis acid catalysts such as aluminum chloride, tin tetrachloride, titanium tetrachloride, trifluoroboron, and trimethylsilyl trifluoromethanesulfonate. The acid catalyst is preferably trimethylsilyl trifluoromethanesulfonate.

The reaction temperature differs depending on the starting compound, solvent, and acid catalyst used and is usually 0° C. to 150° C., preferably 70° C. to 120° C.

The reaction time differs depending on the starting compound, solvent, and acid catalyst used, and the reaction temperature and is usually 0.5 hours to 24 hours, preferably 1 hour to 8 hours.

After the completion of the reaction, the compound (III) of interest of this reaction is obtained, for example, by: concentrating the reaction mixture; adding water and an immiscible organic solvent such as ethyl acetate to the residue; after washing with water, separating the organic layer containing the compound of interest; drying the organic layer over anhydrous magnesium sulfate or the like; and then distilling off the solvent.

The obtained compound can be further purified, if necessary, by a routine method, for example, recrystallization or silica gel column chromatography.

In this step of producing compound (III), the trimethylsilylated compound can also be formed in a reaction system containing compound (IVb) and a trimethylsilylating agent and then reacted with compound (II) in one pot without being isolated.

The trimethylsilylating agent used in the one-pot reaction is, for example, N,O-bis(trimethylsilyl)acetamide (BSA) or 1,1,1,3,3,3-hexamethyldisilazane (HMDS) and is preferably N,O-bis(trimethylsilyl)acetamide.

EXAMPLES

Hereinafter, the present invention will be described more specifically with reference to Examples and Reference Examples.

Example 1

2'-O-Acetyl-3',5'-di-O-benzyl-4'-(2-t-butyldiphenylsilyloxyethyl)-6-N-benzoyladenosine

[Formula 13]

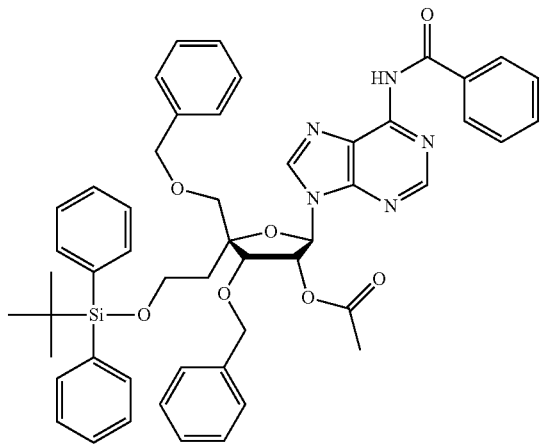

(1) 3,5-di-O-Benzyl-4-(2-t-butyldiphenylsilyloxyethyl)-1,2-O-isopropylidene-α-D-erythropentofuranose 3,5-di-O-Benzyl-4-(2-hydroxyethyl)-1,2-O-isopropylidene-α-D-erythropentofuranose (18.3 g, 44.2 mmol) was dissolved in dry dimethylformamide (DMF, 55 mL). Under a nitrogen stream, imidazole (15.7 g, 218 mmol) was added to this solution, and the mixture was cooled to 0° C. t-Butyldiphenylchlorosilane (23.0 mL, 88.4 mmol) was added thereto, and the mixture was stirred for 15 minutes. After the completion of the reaction, the reaction solution was diluted with ether (ca. 3 mL). A saturated aqueous solution of sodium bicarbonate (ca. 50 mL) was added thereto, and the mixture was concentrated under reduced pressure. Ether and DMF were distilled off. Water (ca. 10 mL) was added to the residue, followed by extraction with ethyl acetate (30 mL×3). The organic layer was washed with saturated saline, dried over anhydrous magnesium sulfate, and then concentrated under reduced pressure. The residue was purified by silica gel column chromatography (elution solvent: hexane/ethyl acetate=5/1) to obtain the title compound (28.8 g).

(2) 3,5-di-O-Benzyl-4-(2-t-butyldiphenylsilyloxyethyl)-1,2-di-O-acetyl-α-D-erythropentofuranose The compound (containing an amount corresponding to 28.8 g, 44.2 mmol) obtained in step (1) was dissolved in acetic acid (150 mL), and this solution was cooled to 0° C. Acetic anhydride (82.2 mL, 871 mmol) and concentrated sulfuric acid (cat. 10 µL) were added thereto, and the mixture was then stirred for 30 minutes. After the completion of the reaction, the reaction solution was put in ice water (50 mL), and the mixture was stirred for 1 hour. Saturated saline (ca. 50 mL) was added thereto, followed by extraction with ethyl acetate (50 mL×3). The organic layer was washed with a saturated aqueous solution of sodium bicarbonate and saturated saline in this order, dried over anhydrous magnesium sulfate, and then concentrated under reduced pressure. The residue was purified by silica gel column chromatography (elution solvent: hexane/ethyl acetate=10/1) to obtain the title compound (mixture of α and β forms, 26.0 g, yield: 84% (2 steps)). The NMR data of the α form obtained by the further purification of a portion of the obtained compound will be shown below.
$^1$H-NMR (400 MHz, CDCl$_3$) δ (ppm): 1.02 (9H, s), 1.84 (3H, s), 1.93 (3H, s), 1.95-2.18 (2H, m), 3.40 (1H, d), 3.50 (1H, d), 3.80-3.93 (2H, m), 4.35-4.60 (5H, m), 5.29 (1H, d), 6.03 (1H, s), 7.20-7.40 (16H, m), 7.60-7.70 (4H, m).

(3) 2'-O-Acetyl-3',5'-di-O-benzyl-4'-(2-t-butyldiphenylsilyloxyethyl)-6-N-benzoyladenosine HMDS (20 mL) and trimethylsilyl chloride (4 mL) were added to N6-benzoyladenine (268 mg, 1.12 mmol), and the mixture was refluxed overnight, concentrated under reduced pressure, and dried to obtain trimethylsilylated N6-benzoyladenine.
The compound (521 mg, 0.748 mmol) obtained in step (2) was dissolved in dry toluene (10 mL). Under a nitrogen stream, the above-mentioned trimethylsilylated N6-benzoyladenine and trimethylsilyl trifluoromethanesulfonate (TMSOTf, 166 µL, 0.901 mmol) were added to this solution, and the mixture was stirred. After 5 minutes, the consumption of the starting material was confirmed by thin-layer chromatography (TLC), followed by heating to reflux for 2 hours. After the completion of the reaction, a saturated aqueous solution of sodium bicarbonate (ca. 2 mL) was added to the reaction solution, and the mixture was filtered through celite. The filtrate was subjected to extraction with dichloromethane (ca. 10 mL). The organic layer was washed with a saturated sodium bicarbonate solution and saturated saline in this order, dried over anhydrous magnesium sulfate, and then concentrated under reduced pressure. The residue was purified by silica gel column chromatography (elution solvent: dichloromethane/methanol=100/1) to obtain the title compound (482 mg, yield: 74%).
$^1$H-NMR (400 MHz, CDCl$_3$) δ (ppm): 1.02 (9H, s), 1.88-1.97 (1H, m), 2.02 (3H, s), 2.15-2.25 (1H, m), 3.44 (1H, d), 3.75-3.90 (3H, m), 4.37-4.61 (5H, m), 5.86 (1H, t), 6.26 (1H, d), 7.20-7.65 (23H, m), 8.03 (2H, d), 8.31 (1H, s), 8.77 (1H, s), 9.04 (1H, s).

Example 2

3',5'-di-O-Benzyl-2'-O-4'-C-ethylene-6-N-benzoyladenosine (1) 2'-O-Acetyl-3',5'-di-O-benzyl-4'-(2-hydroxyethyl)-6-N-benzoyladenosine The compound (475 mg, 0.542 mmol) obtained in Example 1(3) was dissolved in dry tetrahydrofuran (THF, 5 mL). A solution of tetrabutylammonium fluoride in THF (1 mol/L, 705 µL, 0.705 mmol) was added to this solution, and the mixture was stirred at room temperature for 12 hours. After the completion of the reaction, the reaction solution was concentrated under reduced pressure. The residue was purified by silica gel column chromatography (elution solvent: dichloromethane/methanol=50/1) to obtain the title compound (269 mg, yield: 78%).
$^1$H-NMR (400 MHz, CDCl$_3$) δ (ppm): 1.88-1.95 (1H, m), 2.08 (3H, s), 2.20-2.30 (2H, m), 3.47 (1H, d), 3.74 (1H, d), 3.76-3.85 (2H, m), 4.42-4.68 (5H, m), 5.97 (1H, t), 6.35 (1H, d), 7.24-7.65 (13H, m), 8.03 (2H, d), 8.26 (1H, s), 8.76 (1H, s), 9.06 (1H, s).

(2) 3',5'-di-O-Benzyl-2'-O-4'-C-ethylene-6-N-benzoyladenosine

Under a nitrogen stream, the compound (102 mg, 0.106 mmol) obtained in step (1) was dissolved in dry dichloromethane (2 mL), pyridine (100 µL) and methanesulfonyl chloride (36 µL, 0.465 mmol) were added to this solution, and the mixture was stirred at room temperature for 12 hours. Then, water (ca. 1 mL) was added thereto, followed by extraction with dichloromethane (5 mL). The organic layer was washed with saturated saline, dried over anhydrous magnesium sulfate, and then concentrated under reduced pressure. The residue was dissolved in a mixed solvent of pyridine (3 mL) and methanol (2 mL). This solution was cooled to 0° C. A 5 mol/L aqueous sodium hydroxide solution (5 mL) was added thereto, and the mixture was stirred for 10 minutes. After the completion of the reaction, the reaction solution was subjected to extraction with dichloromethane (5 mL×3). The organic layer was washed with a phosphate buffer (pH 6.86, 0.025 M) and saturated saline in this order, dried over anhydrous magnesium sulfate, and concentrated under reduced pressure. The obtained residue was purified by silica gel column chromatography (elution solvent: dichloromethane/methanol=50:1) to obtain the title compound (84.3 mg, yield: 91%). This compound was completely consistent with the compound described in Example 10 of Japanese Patent Laid-Open No. 2000-297097 in analysis by $^1$H-NMR.

Example 3

2'-O-Acetyl-3',5'-di-O-benzyl-4'-(2-t-butyldiphenyl-silyloxyethyl)-2-N-isobutyrylguanosine

[Formula 14]

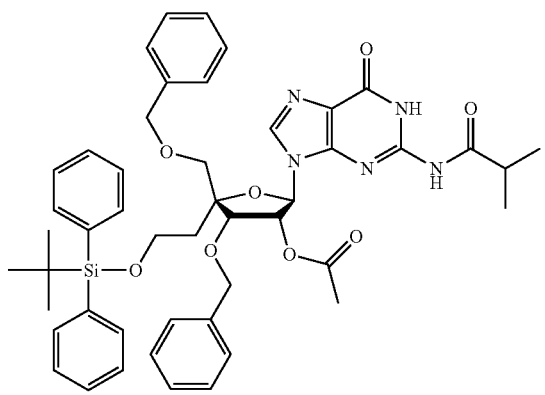

HMDS (500 mL) and trimethylsilyl chloride (125 mL) were added to N2-isobutyrylguanine (7.14 g, 32.3 mmol), and the mixture was refluxed overnight, concentrated under reduced pressure, and dried to obtain trimethylsilylated N2-isobutyrylguanine.

The compound (15.0 g, 21.5 mmol) obtained in Example 1(2) was dissolved in dry toluene (200 mL). Under a nitrogen stream, the above-mentioned trimethylsilylated N2-isobutyrylguanine and TMSOTf (4.80 mL, 26.1 mmol) were added to this solution, and the mixture was stirred. After 5 minutes, the consumption of the starting material was confirmed by TLC, followed by heating to reflux for 2 hours. After the completion of the reaction, a saturated aqueous solution of sodium bicarbonate (ca. 50 mL) was added to the reaction solution, and the mixture was filtered through celite. The filtrate was subjected to extraction with dichloromethane (ca. 300 mL). The organic layer was washed with a saturated sodium bicarbonate solution and saturated saline in this order, dried over anhydrous magnesium sulfate, and then concentrated under reduced pressure. The residue was purified by silica gel column chromatography (elution solvent: dichloromethane/methanol=100/1.5) to obtain the title compound (16.0 g, yield: 86%; which was a mixture containing an isomer glycosylated at the 7-position of guanine).

Example 4

2'-O-Acetyl-3',5'-di-O-benzyl-4'-(2-t-butyldiphenyl-silyloxyethyl)-2-N-isobutyrylguanosine The compound (6.18 g, 8.87 mmol) obtained in Example 1(2) was dissolved in dry toluene (120 mL). Under a nitrogen stream, N2-isobutyrylguanine (2.83 g, 13.3 mmol) and N,O-bis(trimethylsilyl)acetamide (BSA, 9.60 mL, 38.8 mmol) were added to this solution, and the mixture was heated to reflux for 1 hour. Subsequently, TMSOTf (3.40 mL, 18.5 mmol) was added to the reaction solution, and the mixture was further heated to reflux for 45 minutes. After the completion of the reaction, the title compound (6.44 g, yield: 85%; which was a mixture containing an isomer glycosylated at the 7-position of guanine) was obtained in the same way as in Example 3.

Example 5

3',5'-di-O-Benzyl-2'-O-4'-C-ethylene-2-N-isobutyrylguanosine (1) 2'-O-Acetyl-3',5'-di-O-benzyl-4'-(2-hydroxyethyl)-2-N-isobutyrylguanosine The compound (16.0 g, 18.6 mmol) obtained in Example 3 was dissolved in THF (160 mL). A solution of tetrabutylammonium fluoride in THF (1 mol/L, 25 mL, 25.0 mmol) was added to this solution, and the mixture was stirred at room temperature for 12 hours. After the completion of the reaction, the reaction solution was concentrated under reduced pressure. The residue was purified by silica gel column chromatography (elution solvent: dichloromethane/methanol=20/1) to obtain the title compound (9.97 g, yield: 75%; which was a mixture containing an isomer glycosylated at the 7-position of guanine).

(2) 3',5'-di-O-Benzyl-2'-O-4'-C-ethylene-2-N-isobutyrylguanosine

The compound (3.00 g, 4.84 mmol) obtained in step (1) was dissolved in dry dichloromethane (25 mL). Under a nitrogen stream, pyridine (4 mL) and methanesulfonyl chloride (750 μL, 9.69 mmol) were added to this solution, and the mixture was stirred at room temperature for 12 hours. After the completion of the reaction, water (ca. 5 mL) was added thereto, followed by extraction with dichloromethane (ca. 30 mL). The organic layer was washed with saturated saline, dried over anhydrous magnesium sulfate, and then concentrated under reduced pressure. The residue was dissolved in a mixed solvent of pyridine (25 mL) and methanol (10 mL), and the solution was cooled to 0° C. An aqueous sodium hydroxide solution (5 mol/L, 25 mL) was added to this solution, and the mixture was stirred for 30 minutes. Then, the reaction solution was subjected to extraction with a dichloromethane (ca. 50 mL×3) solution. The organic layer was washed with saturated saline, dried over anhydrous magnesium sulfate, and concentrated under reduced pressure. Then, the residue was completely separated and purified from an isomer glycosylated at the 7-position of guanine by silica gel column chromatography (elution solvent: dichloromethane/methanol=100/1.5) to obtain the title compound (1.81 g, yield: 43% (4 steps)). This compound was completely consistent with the compound described in Example 24 of Japanese Patent Laid-Open No. 2000-297097 in analysis by $^1$H-NMR.

Reference Example 1

2'-O-Acetyl-3',5'-di-O-benzyl-4'-(2-t-butyldiphenyl-silyloxyethyl)-5-methyluridine

[Formula 15]

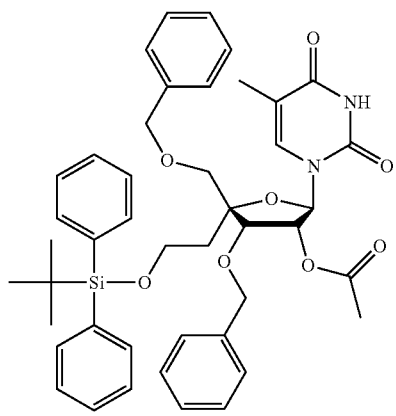

The compound (206 mg, 0.336 mmol) obtained in Example 1(2) was dissolved in dry acetonitrile (4 mL). Under a nitrogen stream, thymine (62.8 mg, 0.498 mmol) and N,O-bis(trimethylsilyl)acetamide (BSA, 0.37 mL, 1.5 mmol) were added to this solution, and the mixture was heated to reflux for 1 hour. Subsequently, TMSOTf (0.125 mL, 0.678 mmol) was added to the reaction solution, and the mixture was further heated to reflux for 40 minutes. After the completion of the reaction, a saturated aqueous solution of sodium bicarbonate was added to the reaction solution, followed by extraction with dichloromethane. The organic layer was washed with saturated saline, dried over anhydrous magnesium sulfate, and then concentrated under reduced pressure. The residue was purified by silica gel column chromatography (elution solvent: hexane/ethyl acetate=1/2) to obtain the title compound (190 mg, yield: 74%).

$^1$H-NMR (400 MHz, CDCl$_3$) δ (ppm): 1.04 (9H, s), 1.47 (3H, s), 1.74-1.85 (1H, m), 2.02 (3H, s), 2.03-2.08 (1H, m), 3.39 (1H, d, J=10.3 Hz), 3.69-3.83 (2H, m), 3.86 (1H, d, J=11 Hz), 4.32-4.56 (5H, m), 5.33 (1H, t), 6.06 (1H, d, J=5.1 Hz), 7.19-7.61 (20H, m), 7.93 (1H, s).

Reference Example 2

3',5'-di-O-Benzyl-2'-O-4'-C-ethylene-5-methyluridine

(1) 2'-O-Acetyl-3',5'-di-O-benzyl-4'-(2-hydroxyethyl)-5-methyluridine

The compound (185 mg, 0.242 mmol) obtained in Reference Example 1 was dissolved in THF (2 mL). A solution of tetrabutylammonium fluoride in THF (1 mol/L, 0.34 mL, 0.34 mmol) was added to this solution, and the mixture was stirred overnight at room temperature. After the completion of the reaction, the reaction solution was concentrated under reduced pressure. The residue was purified by silica gel column chromatography (elution solvent: hexane/ethyl acetate=1/4) to obtain the title compound (121 mg, yield: 95%).

$^1$H-NMR (400 MHz, CDCl$_3$) δ (ppm): 1.49 (3H, s), 1.73-1.80 (1H, m), 2.06 (3H, s), 2.11-2.17 (1H, m), 3.24-3.28 (1H, m), 3.41 (1H, d, J=10.3 Hz), 3.72-3.75 (2H, m), 3.77 (1H, d, J=10.3 Hz), 4.34-4.62 (5H, m), 5.39 (1H, t), 6.16 (1H, d, J=5.1 Hz), 7.20-7.41 (11H, m).

(2) 3',5'-di-O-Benzyl-2'-O-4'-C-ethylene-5-methyluridine

The compound (55.4 mg, 0.106 mmol) obtained in step (1) was dissolved in dry dichloromethane (1 mL). Under a nitrogen stream, pyridine (0.1 mL) and methanesulfonyl chloride (16.5 µL, 0.213 mmol) were added to this solution, and the mixture was stirred at room temperature for 3 hours. After the completion of the reaction, water was added thereto, followed by extraction with dichloromethane. The organic layer was washed with saturated saline, dried over anhydrous magnesium sulfate, and then concentrated under reduced pressure. The residue was dissolved in a mixed solvent of pyridine (0.5 mL) and methanol (0.5 mL), and the solution was cooled to 0° C. An aqueous sodium hydroxide solution (5 mol/L, 1 mL) was added to this solution, and the mixture was stirred for 5 minutes. Then, the reaction solution was subjected to extraction with dichloromethane. The organic layer was washed with saturated saline, dried over anhydrous magnesium sulfate, and concentrated under reduced pressure. Then, the residue was purified by silica gel column chromatography (elution solvent: dichloromethane/methanol=100/1.5→100/2) to obtain the title compound (40.1 mg, yield: 82%). This compound was completely consistent with the compound described in Example 6 of Japanese Patent Laid-Open No. 2000-297097 in analysis by $^1$H-NMR.

INDUSTRIAL APPLICABILITY

According to the present invention, an oligonucleotide analog having stable and excellent antisense or antigene activity or having excellent activity as a detection reagent (probe) for a specific gene or as a primer for initiation of amplification of a specific gene, and intermediate compound (III) for the production of nucleoside analog compound (Ia) or (I) which serves as an intermediate for the production thereof can be produced at high yields regardless of the type of nucleobase.

The invention claimed is:

1. A method of producing a compound of formula (III):

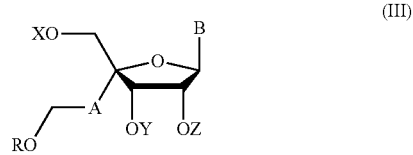

or a salt thereof, comprising
reacting a compound of formula (IVb):

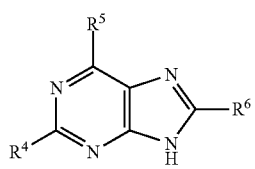

with a trimethylsilylating agent to produce a trimethylsilylated compound; and reacting the trimethylsilylated compound with a compound of formula (II):

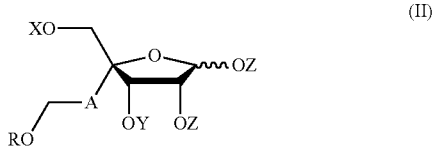

(II)

or a salt thereof,
wherein

A is an alkylene group having 1 to 4 carbon atoms;

B is a purin-9-yl group or a purin-9-yl group having one or more substituents selected from group α;

X, Y, and Z are each independently a protective group for the hydroxy group;

R is a silyl protective group;

$R^4$, $R^5$, and $R^6$ are each independently a hydrogen atom, a hydroxy group, a protected hydroxy group, an alkoxy group having 1 to 4 carbon atoms, a mercapto group, a protected mercapto group, an alkylthio group having 1 to 4 carbon atoms, an amino group, a protected amino group, an amino group substituted by one or more alkyl groups having 1 to 4 carbon atoms, an alkyl group having 1 to 4 carbon atoms, or a halogen atom; and group α is a hydroxy group, a protected hydroxy group, an alkoxy group having 1 to 4 carbon atoms, a mercapto group, a protected mercapto group, an alkylthio group having 1 to 4 carbon atoms, an amino group, a protected amino group, an amino group substituted by one or more alkyl groups having 1 to 4 carbon atoms, an alkyl group having 1 to 4 carbon atoms, or a halogen atom.

2. The method of claim 1, wherein X is a methyl group substituted by 1 to 3 aryl groups, or a methyl group substituted by 1 to 3 aryl groups wherein the aryl rings are each substituted by a lower alkyl, lower alkoxy, halogen, or cyano group.

3. The method of claim 1, wherein X is a benzyl group, a p-methoxybenzyl group, a dimethoxytrityl group, or a monomethoxytrityl group.

4. The method of claim 1, wherein Y is a methyl group substituted by 1 to 3 aryl groups, or a methyl group substituted by 1 to 3 aryl groups wherein the aryl rings are each substituted by a lower alkyl, lower alkoxy, halogen, or cyano group.

5. The method of claim 1, wherein Y is a benzyl group, a β-naphthylmethyl group, or a p-methoxybenzyl group.

6. The method of claim 1, wherein Z is an aliphatic acyl group having 2 to 4 carbon atoms.

7. The method of claim 1, wherein Z is an acetyl group.

8. The method of claim 1, wherein A is a methylene group or an ethylene group.

9. The method of claim 1, wherein A is a methylene group.

10. The method of claim 1, wherein B is a 6-aminopurin-9-yl group, a 6-aminopurin-9-yl group with the amino group protected, a 2,6-diaminopurin-9-yl group, a 2-amino-6-chloropurin-9-yl group, a 2-amino-6-chloropurin-9-yl group with the amino group protected, a 2-amino-6-fluoropurin-9-yl group, a 2-amino-6-fluoropurin-9-yl group with the amino group protected, a 2-amino-6-bromopurin-9-yl group, a 2-amino-6-bromopurin-9-yl group with the amino group protected, a 2-amino-6-hydroxypurin-9-yl group, a 2-amino-6-hydroxypurin-9-yl group with the amino group protected, a 2-amino-6-hydroxypurin-9-yl group with the amino group and hydroxy group protected, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, or a 6-mercaptopurin-9-yl group.

11. The method of claim 1, wherein B is a 6-benzoylaminopurin-9-yl group, an adeninyl group, a 2-isobutyrylamino-6-hydroxypurin-9-yl group, or a guaninyl group.

12. The method of claim 1, wherein R is a tri-lower alkylsilyl group, a monoaryl di-lower alkylsilyl group, or a diaryl mono-lower alkylsilyl group.

13. The method of claim 1, wherein R is a monoaryl di-lower alkylsilyl group or a diaryl mono-lower alkylsilyl group.

14. The method of claim 1, wherein R is a t-butyldiphenylsilyl group.

* * * * *